United States Patent [19]

Roth

[11] 4,019,633
[45] Apr. 26, 1977

[54] CARTONED MEDICAL INSTRUMENT PACKAGE

[75] Inventor: Nathan Roth, San Francisco, Calif.

[73] Assignee: Alza Corporation, Palo Alto, Calif.

[22] Filed: July 18, 1975

[21] Appl. No.: 597,020

[52] U.S. Cl. .................. 206/364; 206/45.14; 206/471; 206/467; 229/8; 229/87 R; 206/815

[51] Int. Cl.² .................. B65D 83/10; B65D 5/50

[58] Field of Search ............ 206/44 R, 45.14, 72, 206/305, 306, 349, 363, 364, 465, 467, 420–428, 815; 229/40, 8, 87 R, 2.5

[56] References Cited

UNITED STATES PATENTS

| | | | |
|---|---|---|---|
| 3,618,848 | 11/1971 | Pawlowski et al. | 206/45.14 |
| 3,866,745 | 2/1975 | Dlugopolski | 206/45.14 |
| 3,929,222 | 12/1975 | Smith et al. | 206/45.14 |

FOREIGN PATENTS OR APPLICATIONS

| | | | |
|---|---|---|---|
| 741,173 | 8/1966 | Canada | 206/306 |

*Primary Examiner*—William Price
*Assistant Examiner*—Douglas B. Farrow
*Attorney, Agent, or Firm*—Thomas E. Ciotti; Paul L. Sabatine; Edward L. Mandell

[57] ABSTRACT

A package for an intrauterine device-intrauterine device inserter combination and a "pillow pack" carton for the package are disclosed. The package consists of three elements: (1) a thermoformed plastic tray having an elongated, relatively deep cavity for holding the combination, a convexly curved marginal ledge about the cavity, an end wall extending downwardly from each end of the ledge, and a flange extending outwardly from the bottom of each end wall; (2) a cover that fits over the cavity and has the same curvature as the marginal ledge; and (3) an adhesive coating on the inner side of the cover by which the cover is attached to the ledge over the cavity. The package is enveloped in a paper carton that has a bottom wall on which the package bottom rests, a pair of end walls, each of which has an inwardly extending section that overlies one of the flanges of the package tray whereby the package is held firmly in place, and a pair of flaps that are foldably connected to the longitudinal edges of the bottom wall and fold over the top of the package in an overlapping, interlocking fashion.

5 Claims, 8 Drawing Figures

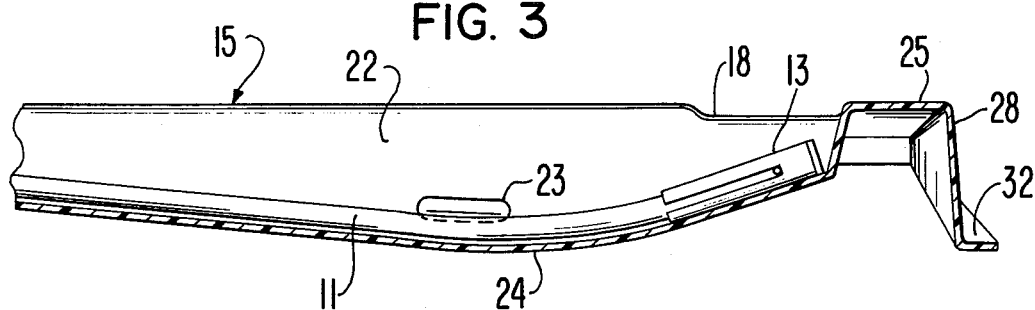
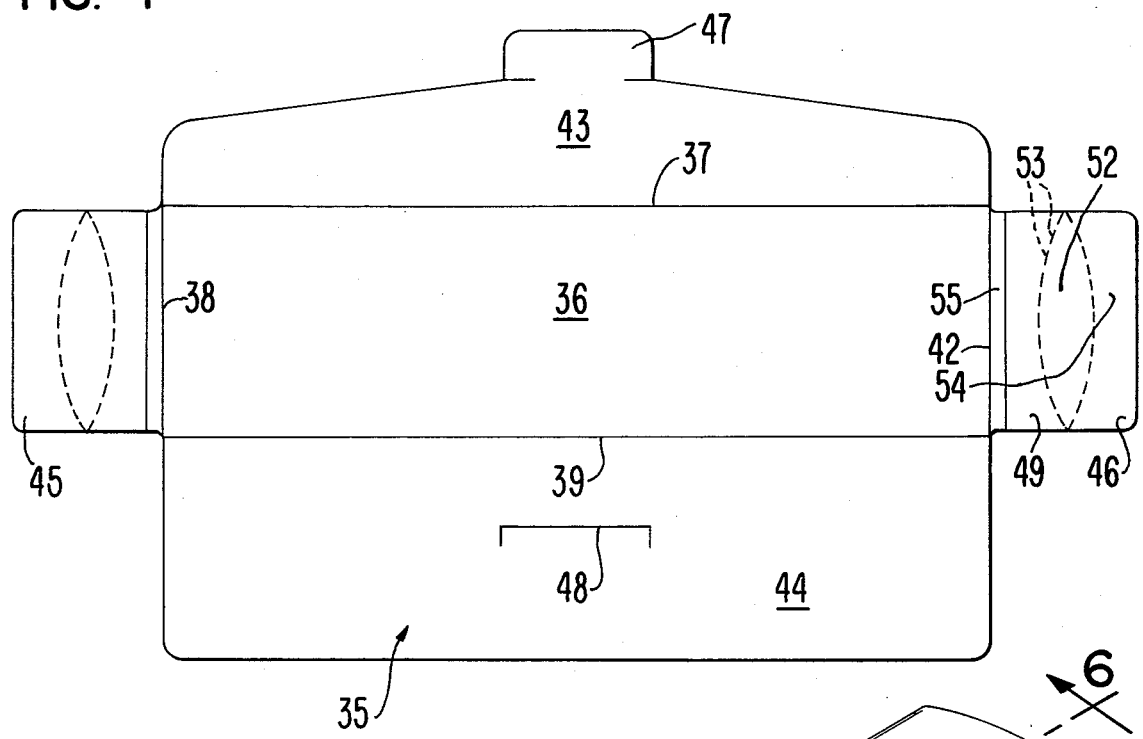
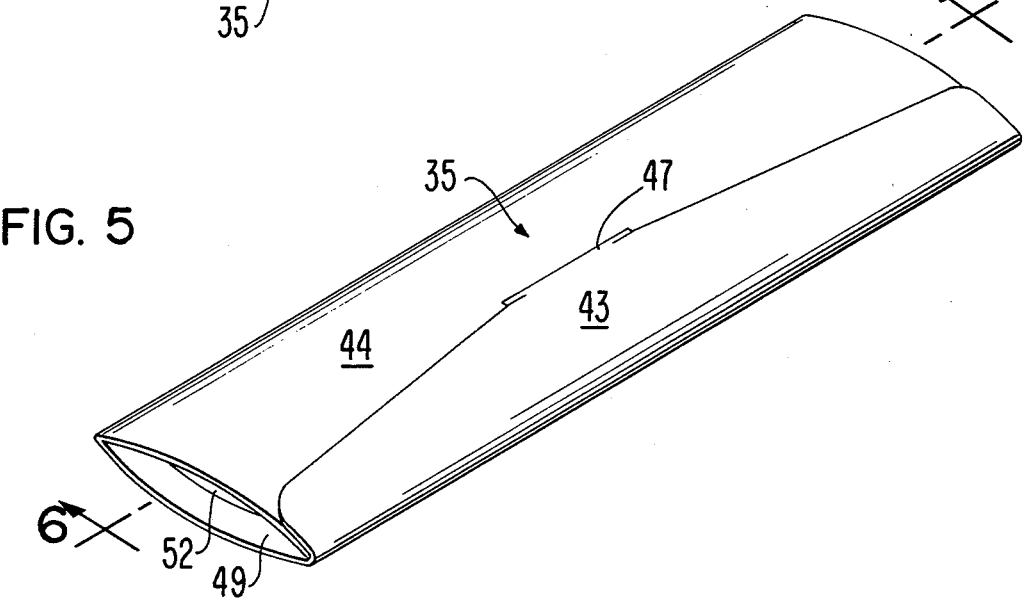

CARTONED MEDICAL INSTRUMENT PACKAGE

BACKGROUND OF THE INVENTION

1. Field of the Invention

The invention relates to a medical instrument package and to a cartoned medical instrument package.

2. Description of the Prior Art

Various types of medical instrument packages are known in the art. One type is basically a heat sealed, sterilized envelope formed from sheets of plastic, such as polyethylene. Such packages are described in U.S. Pat. Nos. 3,123,210; 3,398,737; 3,419,137; 3,448,737; and 3,595,465.

Another type consists of a cardboard tray or carton. Examples of this type of package appear in U.S. Pat. Nos. 3,411,620 and 3,746,152.

A third type of medical instrument package consists of a so-called "blister pack" and is the most relevant to the present invention. These packages usually consist of two elements: a plastic thermoformed casing or tray having a cavity in which the instrument is held, and a cardboard or plastic cover that is heat sealed onto the top of the casing or tray over the cavity. Packages of this type are disclosed in U.S. Pat. Nos. 3,035,691; 3,353,664; 3,435,944; and 3,755,042.

U.S. Pat. No. 3,767,105 teaches "pillow pack" cartons that are relative to the carton portion of the invention.

SUMMARY OF THE INVENTION

One aspect of the invention is a medical instrument package comprising: a thermoplastic tray having a cavity for holding the instrument, at least a portion of the cavity being deeper than it is wide, and a convexly curved marginal ledge about said cavity; a cover for said cavity that has the same curvature as said marginal ledge; and means, such as an adhesive coating, interposed between the cover and ledge for adhesively securing the cover to the ledge about the complete perimeter of the cavity such that the cover may be peeled away from said ledge to expose the cavity.

A second aspect of the invention is a cartoned medical instrument package comprising in combination: the above described medical instrument package wherein the tray has an end wall extending downwardly from each end of the ledge, and a flange extending outwardly from the bottom of each end wall; and a carton adapted to envelop the package comprising a bottom wall against which the bottom of the package rests, a pair of end walls, each of which has an inwardly extending section that overlies one of the flanges of the tray of the package whereby the package is held firmly in place in the carton, a first flap foldably connected to one edge of the bottom wall, a second flap foldably connected to an opposite edge of the bottom wall, said first and second flaps adapted to fold over the top of the package in overlapping relationship to each other, and, means for releasably interconnecting said first and second flaps while they are in said overlapping relationship.

In a preferred embodiment of the cartoned medical instrument package, the carton when enclosed about the package has the general shape of an elongated pillow comprising arcuate longitudinal top and bottom surfaces of substantially the same but opposite curvature that are defined by the first and second flaps and the bottom wall, respectively, and a pair of almond-shaped end surfaces extending between said top and bottom surfaces and indented relative to the end thereof that are defined by the end walls of the carton.

BRIEF DESCRIPTION OF THE DRAWINGS

In the drawings:

FIG. 3 is a partial, vertical, sectional view of the package (without its cover) and instrument of FIG. 1;

FIG. 4 is a diminished, top, plan view of a carton (unfolded) in which the package and instrument of FIG. 1 are enclosed;

FIG. 5 is a diminished, dimetric view of a cartoned package, namely the combination of the package of FIG. 1 and the carton of FIG. 4;

DETAILED DESCRIPTION OF THE INVENTION

Figure 1:
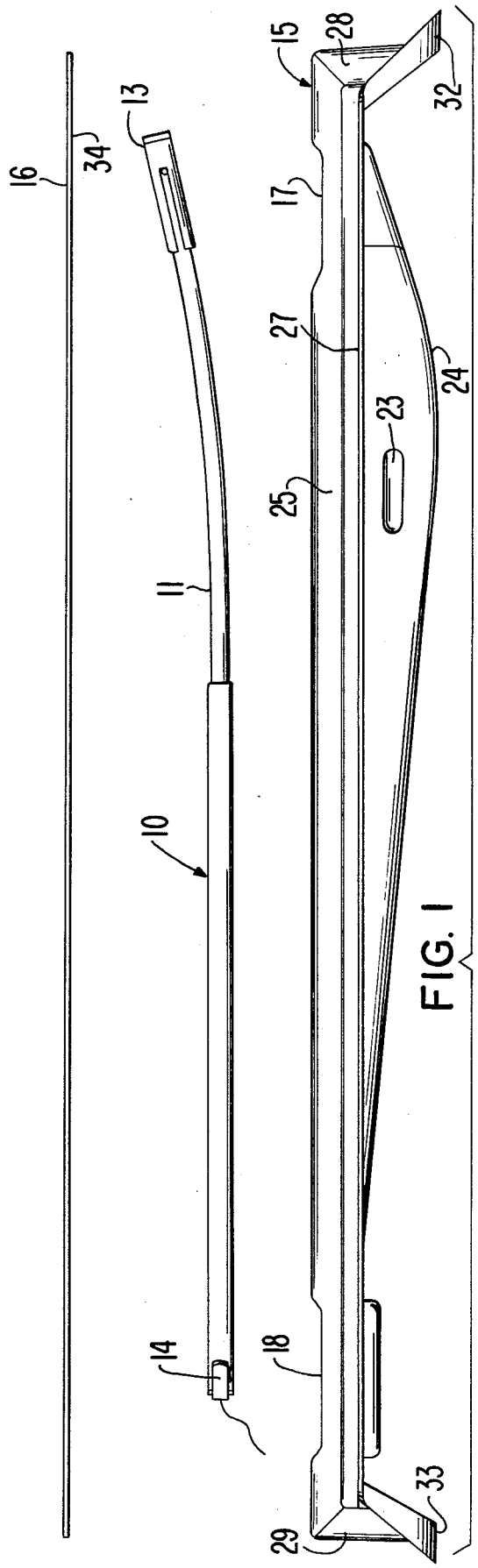
FIG. 1 is an exploded, side, elevational view of an embodiment of the package of the invention, including the medical instrument it is adapted to hold.
Figure 2:
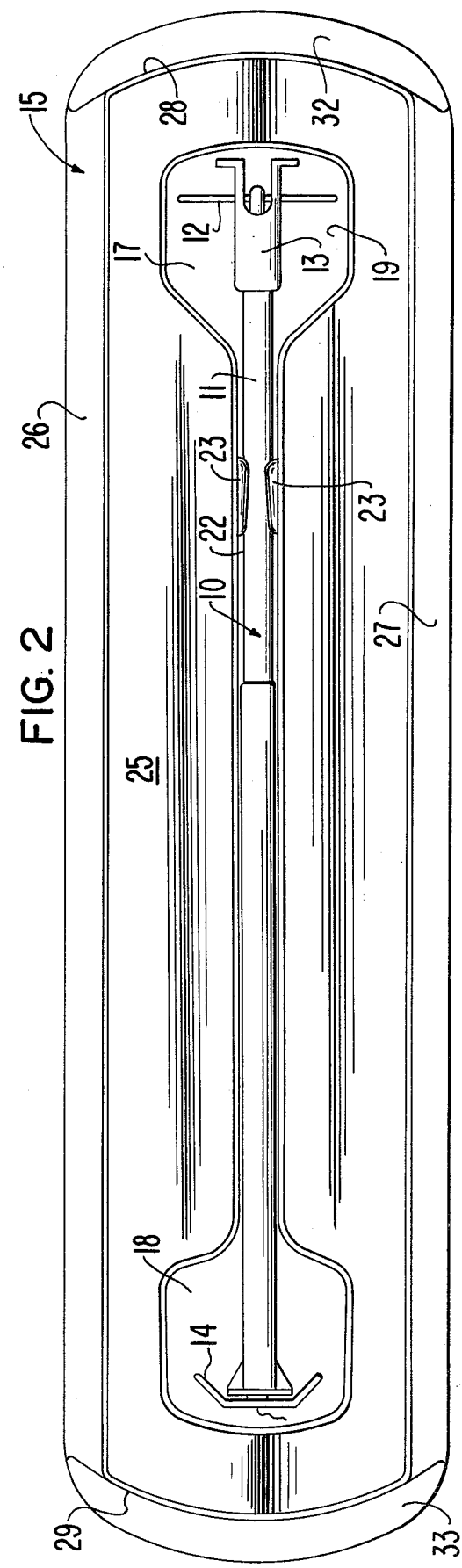
FIG. 2 is a top, plan view of the package and instrument of FIG. 1.

The cartoned package shown in the drawings is for an intrauterine device (IUD-intrauterine device inserter combination, generally designated 10. IUD-inserter combination 10 is not part of the invention and therefore is not described in detail. Combination 10 is the subject of commonly owned application Ser. No. 455,237, filed Mar. 27, 1974. As seen in FIGS. 1 and 2, combination 10 consists basically of an elongated, curved inserter tube 11 with a T-shaped IUD 12 and a cap 13 mounted on one of its ends and a plug 14 mounted in its other end. Combination 10 is intended to be gripped by the doctor at its plugged end during use.

Referring to FIGS. 1-3, the package for combination 10 consists of two elements: a thermoformed, elongated tray, generally designated 15 and a cover 16. Tray 15 has a longitudinal, central, dumbbell-shaped cavity 17 into which IUD-inserter combination 10 fits. Cavity 17 comprises two enlarged end sections 18, 19 interconnected by a thin, central section 22 (FIG. 2). Section 18 accomodates the plugged end of combination 10, section 19 accomodates the cap-IUD end of combination 10, and section 22 accomodates the major portion of inserter tube 11. End section 18 is sufficiently large to provide finger access to the plugged end of combination 10 gripping the combination and removing it from cavity 17.

The depth of cavity 17 varies over its length (FIG. 1) to provide for the curvature of inserter tube 11. Central section 22 of cavity 17 is generally deeper than it is wide. Section 22 is provided with a pair of transversely extending, opposed detents 23 near its deepest point 24. Detents 23 serve as a means to removably snaplock combination 10 into cavity 17. As shown in FIG. 3, when combination 10 is in its locked position within cavity 17, the portion of inserter tube 11 at point 24 is seated beneath detents 23.

A convexly, transversely curved marginal ledge 25 surrounds the opening of cavity 17. Ledge 25 defines the top surface of tray 15 and provides a site for attaching cover 16 over cavity 17. The longitudinal sides of ledge 25 are flanked by flat, depressed shoulders 26, 27, respectively. When cover 16 is affixed to ledge 25 over cavity 17, its edges overlie shoulders 26, 27 so that cover 16 may be easily gripped along its edges to peel it away from the tray 15.

Tray 15 includes a pair of end walls 28, 29 that extend downwardly from ledge 25 and shoulders 26, 27. Walls 28 and 29 are curved transversely at the same degree but opposite relative to each other. The bottom edges of walls 28 and 29 are curved in the same degree as ledge 25 but opposite thereto. Each of walls 28 and 29 has a lip or flange, 32, 33, respectively, that extends longitudinally outwardly from its bottom edge. The outer edges of lips 32, 33 have the same transverse curvature as walls 28, 29, respectively. As described below, lips 32, 33 serve to engage the carton of FIG. 4 to hold the package in place within the carton.

Tray 15 may be made from any of the thermoplastic materials that are used to form "blister pack" containers. Preferably, it is made from polystyrene or the thermoformable acrylic multipolymers sold under the trade designation, "XT Polymer". It may be formed from such thermoplastics by injection molding or thermoforming (either positive pressure or vacuum), preferably by positive pressure thermoforming.

Because of the depth and width of section 22 of cavity 17, it has been found advantageous to form cavity 17 by pressing a sheet of the thermoplastic material over protrusions on a die (rather than by pressing the sheet into deep recesses within a die) and to have the die surface adjacent to the protrusion over which cavity 17 is formed curved. By using this technique, the formation of thin weak areas in the thermoplastic sheet may be avoided.

Cover 16 may be made from a variety of porous or nonporous materials such as paper, plastic films, either continuous or nonwoven, metal foils, and combinations thereof. Nonwoven polyethylene sheeting sold under the trade designation "Tyvek", is preferred. Side 34 of cover 16 has a thin coating 31 (FIG. 1) of an adhesive or sealant that enables the cover to be adhesively secured to ledge 25. Preferably, coating 16 is made of a heat sealant, such as ethylvinyl acetate, so that cover 16 may be secured or bonded to tray 15 by pressing the tray-cover assembly between an appropriately shaped backing plate and an appropriately shaped heating sealing head.

FIG. 4 shows a carton (not folded), generally designated 35, in which the package of FIGS. 1-3 is enclosed. Carton 35 consists of a single piece of heavy paper that is scored into several sections. The several sections of carton 35 are: a bottom wall 36 defined by scores 37, 38, 39 and 42; a first flap 43 adjacent wall 36 along score 37; a second flap 44 adjacent wall 36 along score 39; and two end walls 45, 46 adjacent the respective ends of wall 36 along scores 38, 42. Flap 43 has a tab 47 at the middle of its outer edge, and flap 44 has a slit 48 in it that is adapted to receive tab 47 when the carton is folded about the package and closed. End walls 45, 46 are structurally identical and each has three sections: an inner or bottom section 49 adjacent scores 38 and 42 respectively; a middle, almond-shaped center section 52 defined by elongated perforations 53; and an outer or top section 54. Inner sections 49 each have a strip of adhesive 55 adjacent scores 38, 42 by which they are secured to bottom wall 36.

FIGS. 5-8 illustrate the way in which the package of FIGS. 1-3 is enclosed in carton 35. As seen in FIG. 5, carton 35 folds into a "pillow pack" configuration. In that configuration, sections 49 of end walls 45, 46 fold inwardly from score lines 38, 42, and the innermost edges of sections 49 are adhesively secured to bottom wall 36 (FIG. 6) by adhesive 55. Middle sections 52 are folded relative to sections 49, 54 along perforations 53 and stand generally upright; and outer sections 54 fold outwardly from the outer line of perforations 53. Accordingly, middle sections 52 are indented from the carton ends, and wall 36 and sections 49 and 54 are curved when the carton is folded.

Figure 6:
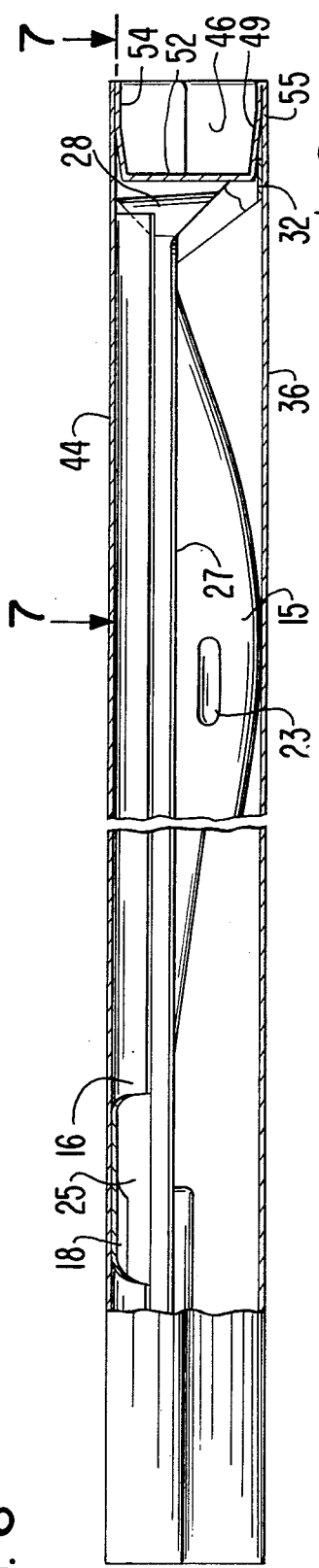
FIG. 6 is an enlarged, sectional view taken along line 6—6 of FIG. 5.
Figure 7:
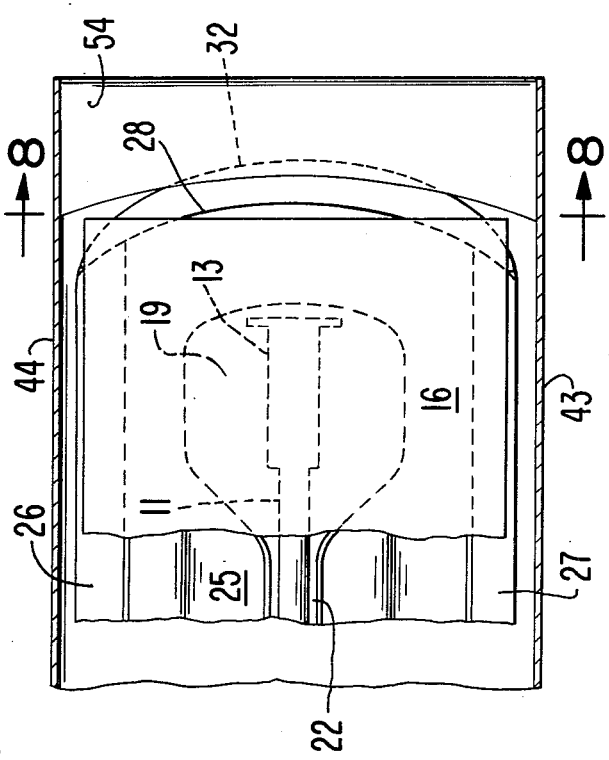
FIG. 7 is a sectional view taken along line 7—7 of FIG. 6.
Figure 8:
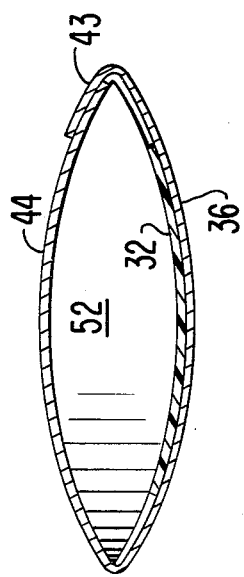
FIG. 8 is a sectional view taken along line 8—8 of FIG. 7.

As best illustrated in FIG. 6, the package of FIGS. 1-3 sits in carton 35 with the portion of its bottom at approximately 24 resting against bottom wall 36. Segments of each of lips 32, 33 also rest on bottom wall 36 of carton 35, and those segments underlie sections 49 of end walls 46 and 45 respectively of carton 35. This causes the package to be held firmly in place within the carton such that it cannot slip or fall out of the carton even if the carton is tipped or turned over. Once the package is so positioned in carton 35, flaps 44, 43 are folded at score lines 39, 37, respectively, over the top of the package, with flap 43 overlapping flap 44 to close the carton. Tab 47 of flap 43 is then slipped into slit 48 to releasably interconnect the flaps and to keep the carton closed.

Modifications of the package and carton described above that are obvious to those skilled in the packaging art and related arts, are intended to be within the scope of the following claims.

I claim:

1. A cartoned medical instrument package comprising in combination:
  a. a package comprising:
    i. a thermoplastic tray having a cavity for holding the instrument, a convexly curved marginal ledge about the cavity extending outwardly from the opening of the cavity and defining the top surface of the tray, an end wall extending downwardly from each end of the ledge, and a flange extending outwardly from the bottom of each end wall,
    ii. a cover for said cavity, and
    iii. means for adhesively securing the cover to said ledge about the complete perimeter of the cavity such that the cover may be peeled away to expose the cavity; and
  b. a carton adapted to envelop the package completely comprising:
    i. a bottom wall against which the bottom of the package rests,
    ii. a pair of single piece end walls, each of which is foldably connected to the bottom wall and has an inwardly extending section that overlies one of the flanges of the tray of the package whereby the package is held firmly in place in the carton,
    iii. a first flap foldably connected to an opposite edge of the bottom wall, said first and second flaps adapted to fold over the top of the package in overlapping relationship to each other, and
    v. means for releasably interconnecting said first and second flaps while they are in said overlapping relationship.

2. The cartoned medical instrument package of claim 1 wherein each end wall of the carton includes a bottom section that folds inwardly from an end of the bottom wall and overlies said flange, a generally upright middle section, and a top section that folds outwardly from the top of the middle section.

3. The cartoned medical instrument package of claim 1 wherein the carton when enclosed about the package has the general shape of an elongated pillow comprising arcuate longitudinal top and bottom surfaces of substantially the same but opposite curvature that are defined by the first and second flaps and the bottom wall, respectively, and a pair of almond-shaped end surfaces extending between the top and bottom surfaces and indented relative to the ends of the top and bottom surfaces that are defined by said end walls.

4. The cartoned medical instrument package of claim 3 wherein the flange has substantially the same but opposite curvature as the marginal ledge, said inwardly extending section and said bottom surface have substantially the same curvature as the flange, and said top surface has substantially the same curvature as the marginal ledge.

5. The cartoned medical instrument package of claim 1 wherein the means for releasably interconnecting the first and second flaps includes a tab on the first flap and a slit in the second flap that is adapted to receive the tab.

* * * * *